US010292726B2

(12) United States Patent
O'Neil et al.

(10) Patent No.: US 10,292,726 B2
(45) Date of Patent: May 21, 2019

(54) TISSUE REMOVAL DEVICES AND METHODS

(71) Applicant: DePuy Synthes Products, Inc., Raynham, MA (US)

(72) Inventors: Michael O'Neil, West Barnstable, MA (US); Zoher Bootwala, Foxboro, MA (US); J. Riley Hawkins, Cumberland, RI (US)

(73) Assignee: DePuy Synthes Products, Inc., Raynham, MA (US)

( * ) Notice: Subject to any disclaimer, the term of this patent is extended or adjusted under 35 U.S.C. 154(b) by 458 days.

(21) Appl. No.: 15/073,226

(22) Filed: Mar. 17, 2016

(65) Prior Publication Data

US 2017/0265881 A1    Sep. 21, 2017

(51) Int. Cl.
   *A61B 17/32*    (2006.01)
   *A61B 17/16*    (2006.01)
   *A61B 17/00*    (2006.01)

(52) U.S. Cl.
   CPC ........ *A61B 17/32002* (2013.01); *A61B 17/32* (2013.01); *A61B 2017/00685* (2013.01); *A61B 2017/320024* (2013.01); *A61B 2017/320028* (2013.01); *A61B 2017/320064* (2013.01); *A61B 2217/005* (2013.01); *A61B 2217/007* (2013.01)

(58) Field of Classification Search
   CPC .. A61B 17/32002; A61B 2017/320024; A61B 17/1604; A61B 17/1606; A61B 17/1608; A61B 17/1611; A61B 2017/320064
   See application file for complete search history.

(56) References Cited

U.S. PATENT DOCUMENTS

| 5,569,284 | A | * | 10/1996 | Young | ............... A61B 17/32002 604/22 |
| 8,230,867 | B2 | | 7/2012 | Mark | |
| 8,486,097 | B2 | | 7/2013 | Mark et al. | |
| 2006/0224160 | A1 | * | 10/2006 | Trieu | ................. A61B 17/1608 606/83 |
| 2010/0179557 | A1 | | 7/2010 | Husted | |

(Continued)

FOREIGN PATENT DOCUMENTS

WO    2013/016698 A1    1/2013

OTHER PUBLICATIONS

International Search Report and Written Opinion for Application No. PCT/US2017/022452, dated May 26, 2017 (15 pages).

(Continued)

*Primary Examiner* — Matthew J Lawson
(74) *Attorney, Agent, or Firm* — Nutter McClennen & Fish LLP

(57) ABSTRACT

Devices and methods for tissue removal are disclosed herein, including those in which a powered rotary tool actuates a cutting blade to sever tissue and drives an auger to transport the severed tissue proximally through the device. The severed tissue can be collected in an on-board collection chamber for subsequent use as graft material or otherwise (e.g., assay, analysis, post-processing, etc.). Devices of the type disclosed herein can reduce or eliminate the need to move the device in and out of the surgical site, reduce user input force, and provide improved ergonomics and increased user focus.

15 Claims, 7 Drawing Sheets

(56) References Cited

U.S. PATENT DOCUMENTS

| | | |
|---|---|---|
| 2012/0004595 A1 | 1/2012 | Dubois et al. |
| 2012/0046682 A1 | 2/2012 | Nelson et al. |
| 2013/0023882 A1* | 1/2013 | Fabro .................. A61B 17/295 606/80 |
| 2013/0046316 A1 | 2/2013 | Sullivan et al. |
| 2014/0277043 A1* | 9/2014 | Jenkins .............. A61B 17/3205 606/170 |

OTHER PUBLICATIONS

[No Author Listed] Aesculap Neurosurgery. Pneumatic Kerrison. Kairison. Aesculap, Inc., 2008, 12 pages.

[No Author Listed] Anspach High Speed. Synthes, Inc. Retrieved from <http://www.synthes.com/sites/NA/Products/PowerTools/AnspachHighSpeed/Pages/default.aspx>. 2014, 3 pages.

[No Author Listed] Powered Bone Management. Aesculap, Inc., 2011, 12 pages.

Echeverri, D., et al., Dissolution of connective tissue in sodium hypochlorite alone an in combination with 3% hydrogen peroxide. Int. J. Odontostomat., 6(3):263-266, 2012.

Forst, L., et al., Carpal tunnel syndrome in spine surgeons: a pilot study. Arch Environ Occup Health. Nov.-Dec. 2006;61(6):259-62.

Maroon, J.C., et al., Pneumatic Kerrison rongeur: technical note. Surg Neurol. Apr. 2009;71(4):466-8. doi: 10.1016/j.surneu.2008.10.008. Epub Jan. 14, 2009.

Stojicic, S., et al., Tissue dissolution by sodium hypochlorite: effect of concentration, temperature, agitation, and surfactant. J Endod. Sep. 2010;36(9):1558-62. doi: 10.1016/j.joen.2010.06.021.

Wadachi, R., et al., Effect of calcium hydroxide on the dissolution of soft tissue on the root canal wall. J Endod. May 1998;24(5):326-30.

* cited by examiner

TISSUE REMOVAL DEVICES AND METHODS

FIELD

Devices and methods for removing tissue are disclosed herein. For example, devices and methods for removing bone tissue during spinal surgery are disclosed.

BACKGROUND

A number of devices have been developed to facilitate tissue removal during a medical procedure. For example, a Kerrison rongeur device or "Kerrison" can be used for cutting, gouging, or biting bone in a surgical procedure. Kerrisons are often used in orthopedic surgery (e.g., to remove vertebral bone in spinal posterior decompression procedures), in neurosurgery (e.g., to remove bone from the skull), and in many other surgeries such as maxillofacial and podiatric surgery.

Existing Kerrisons generally suffer from poor ergonomics which can create strain, discomfort, or fatigue for the surgeon, prolong the length of a procedure, and/or increase risks for the patient. In particular, the design of the device's handles, the high degree of force required to squeeze the handles, the repeated squeezing required, and the height of the surgeon's hand/forearm during use can all contribute to strain on the surgeon. These issues can be exacerbated by the fact that Kerrisons are often used during the most demanding parts of the surgery, such as when the surgeon is removing bone adjacent to the spinal cord or nerve roots, when a high degree of focus and mental stress is put on the surgeon.

Use of existing Kerrisons can also be inefficient and distracting, since they must be repeatedly removed from the surgical site, handed off to an assistant, manually cleared of excised tissue, handed back to the surgeon, and reinserted to the surgical site. The surgeon is thus required to continually shift focus away from the surgical site, and then refocus on the surgical site and re-locate the device to an area that is often very close to sensitive neural or vascular tissue. The surgical site can also be deep down a narrow cannula, which can make it even more difficult to re-locate the area where the device was being used before being removed to clear excised tissue.

There is a continual need for improved tissue removal devices and methods.

SUMMARY

Devices and methods for tissue removal are disclosed herein, including those in which a powered rotary tool actuates a cutting blade to sever tissue and drives an auger to transport the severed tissue proximally through the device. The severed tissue can be collected in an on-board collection chamber for subsequent use as graft material or otherwise (e.g., assay, analysis, post-processing, etc.). Devices of the type disclosed herein can reduce or eliminate the need to move the device in and out of the surgical site, reduce user input force, and provide improved ergonomics and increased user focus.

In some embodiments, a tissue cutting device includes a footplate; a blade having a cutting surface, wherein the blade is movable relative to the footplate between an open position in which a tissue opening is formed between the cutting surface and the footplate and a closed position in which the cutting surface contacts or approaches the footplate to cut tissue disposed therebetween; an auger disposed in a lumen of the device and configured to transport tissue cut by the blade proximally through the lumen; and an input shaft, wherein rotation of the input shaft is effective to rotate the auger and reciprocate the blade between the open and closed positions.

The lumen can be formed in the blade. The lumen can be formed in an outer shaft of the device, and/or the blade can be slidably disposed in the outer shaft. The blade can include an elongate body portion and a basket pivotally coupled to a distal end of the body portion. The blade can include a tubular cannulated body with a sharpened distal-facing surface that defines the cutting surface. The device can include a tissue collection chamber mounted to the device and in fluid communication with the lumen. The tissue collection chamber can be mounted to an outer shaft of the device. The tissue collection chamber can include a first prong that extends through an opening in the outer shaft to wipe tissue from the blade. The tissue collection chamber can include a second prong that extends through the opening in the outer shaft and through an opening formed in the blade to wipe tissue from the auger. The input shaft can be connected to the auger by gears that scale rotation of the auger relative to rotation of the input shaft. The input shaft can be connected to a blade drive assembly that converts rotational movement of the input shaft into longitudinal reciprocating movement of the blade. The blade drive assembly can include a first linkage bar having a first end eccentrically coupled to a rotating shaft and a second end coupled to a rocker arm such that rotation of the rotating shaft alternately rotates the rocker arm clockwise and counterclockwise to alternately advance and retract the blade. A shaft of the auger can include a plurality of modular sections with different profiles configured to mix, shear, or grind tissue. The device can include an aspiration port through which vacuum suction can be applied to an interior of the lumen. The device can include an irrigation port through which fluid can be supplied to an interior of the lumen. The tissue collection chamber can include a neck portion having a longitudinal axis that extends substantially perpendicular to a longitudinal axis of the blade and a canister portion in fluid communication with the neck portion.

In some embodiments, a method of cutting tissue includes positioning tissue within a tissue opening of a tissue cutting device having a blade and a footplate, the tissue opening being defined between a cutting surface of the blade and the footplate; and actuating a rotating drive system to: (i) reciprocate the blade towards and away from the footplate, thereby cutting tissue disposed in the tissue opening; and (ii) rotate an auger of the device to transport cut tissue proximally through the device to a tissue collection chamber.

The rotating drive system can include an electric or pneumatic drill or driver. The method can include applying suction to an interior of the device to pull the cut tissue towards the tissue collection chamber. The method can include delivering fluid to an interior of the device to irrigate tissue moving through the device or dissolve soft tissue from bone tissue moving through the device. The method can include packing tissue collected in the tissue collection chamber into a fusion cage or bone opening of a patient.

BRIEF DESCRIPTION OF THE DRAWINGS

The following detailed description is provided in conjunction with the accompanying drawings, in which.

DETAILED DESCRIPTION

Devices and methods for tissue removal are disclosed herein, including those in which a powered rotary tool actuates a cutting blade to sever tissue and drives an auger to transport the severed tissue proximally through the device. The severed tissue can be collected in an on-board collection chamber for subsequent use as graft material or otherwise (e.g., assay, analysis, post-processing, etc.). Devices of the type disclosed herein can reduce or eliminate the need to move the device in and out of the surgical site, reduce user input force, and provide improved ergonomics and increased user focus.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments. The features illustrated or described in connection with one exemplary embodiment may be combined with the features of other embodiments.

Figure 1:
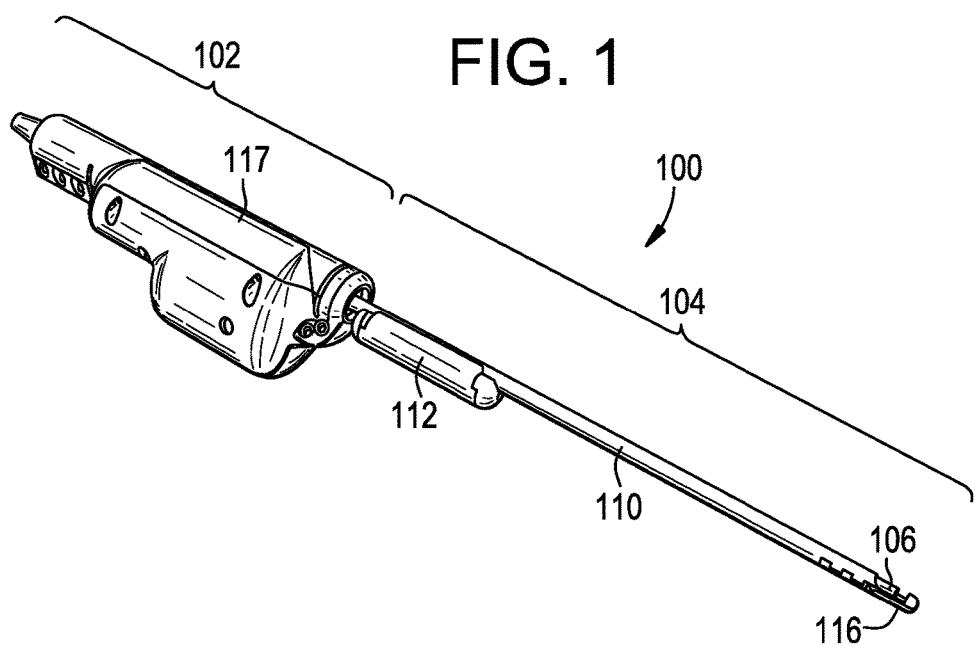
FIG. 1 is a perspective view of a tissue removal device.

FIG. 1 illustrates an exemplary embodiment of a tissue removal device 100. As shown, the device can include a proximal drive assembly 102 and an elongate cutting assembly 104 that extends distally from the proximal drive assembly. The cutting assembly 104 can include a blade 106 configured to cut tissue and an auger 108 or other component configured to transport cut tissue proximally through an outer shaft 110 of the device to a tissue collection chamber 112. The drive assembly 102 can include components for controlling rotation of the auger 108 and movement of the blade 106. The device 100 can be driven by a powered rotary tool (e.g., an electric or pneumatic drill or driver, such as the one shown in FIG. 15) which can advantageously eliminate or reduce surgeon fatigue associated with manual devices. As detailed below, the device 100 can provide improved user ergonomics, accuracy, speed, efficiency, and/or user focus.

Figure 2:
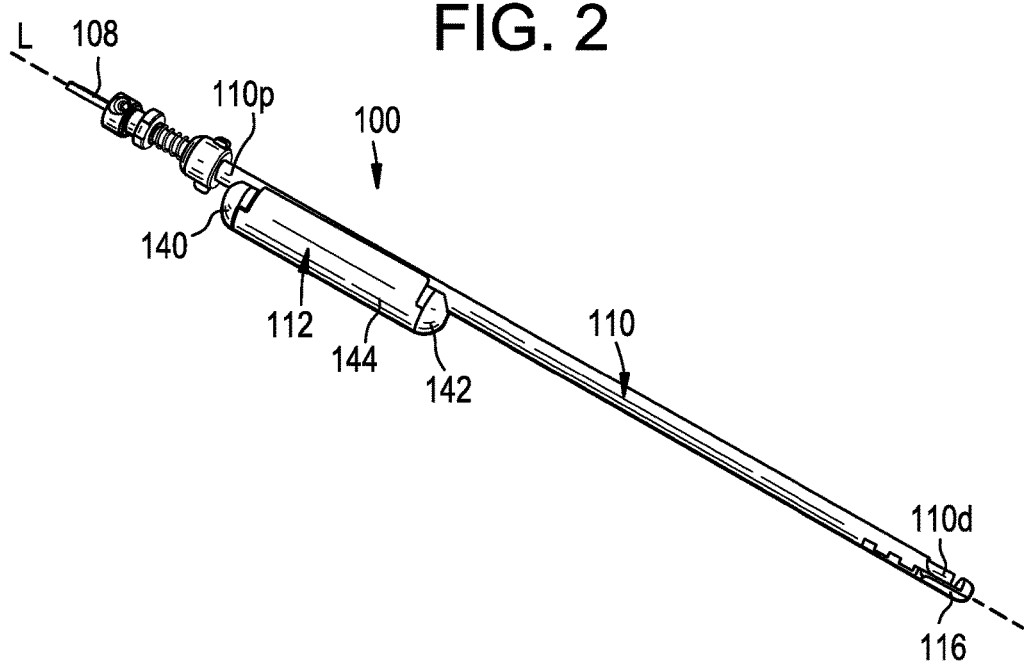
FIG. 2 is a perspective view of the cutting assembly of the tissue removal device of FIG. 1.
Figure 3:
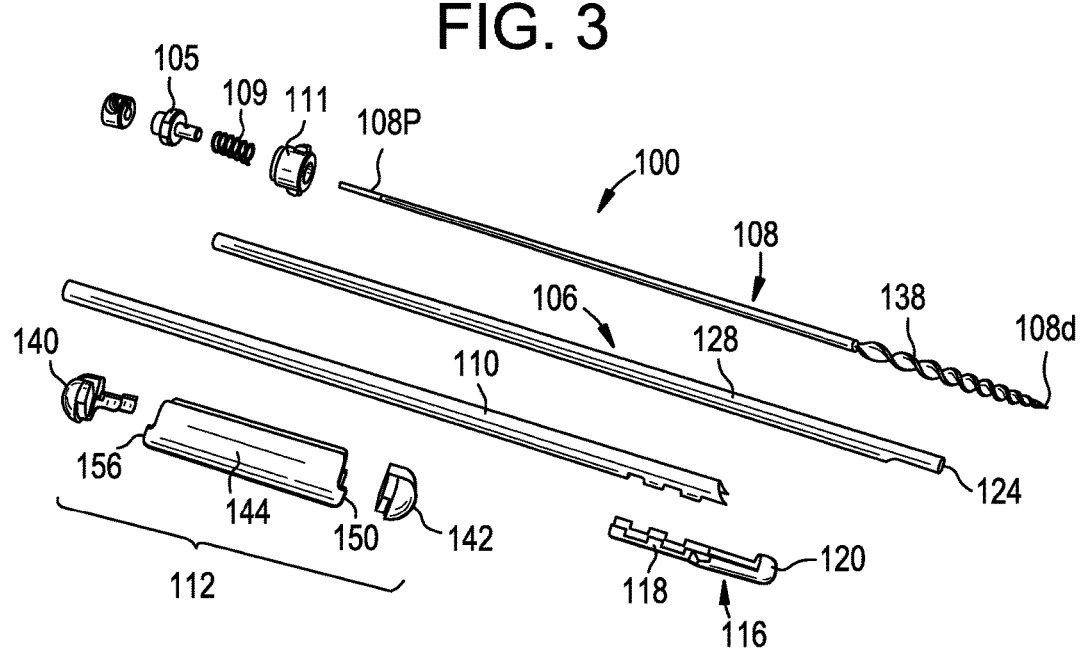
FIG. 3 is an exploded perspective view of the cutting assembly of the tissue removal device of FIG. 1.

FIGS. 2-3 illustrate the cutting assembly 104 of the device 100 in greater detail. The assembly 104 can include an outer shaft 110 that extends along a longitudinal axis L between a proximal end 110*p* and a distal end 110*d*. The shaft 110 can be tubular with a circular transverse cross-section as shown, or can have a variety of other cross-sectional shapes such as square, rectangular, etc. As described further below, a window 114 can be formed adjacent the proximal end 110*p* of the outer shaft 110 to allow tissue conveyed through the shaft to exit the shaft and move into the collection chamber 112. The outer shaft 110 can remain substantially stationary during a tissue cutting procedure, protecting the surrounding tissue or working channel from the moving internal parts of the device 100 and supporting the internal parts of the device.

Figure 4:
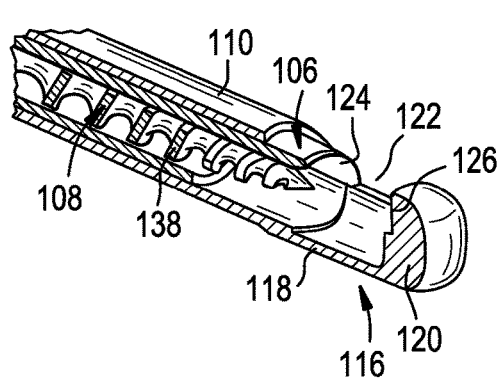
FIG. 4 is a sectional perspective view of the distal tip of the tissue removal device of FIG. 1, shown in an open configuration.
Figure 5:
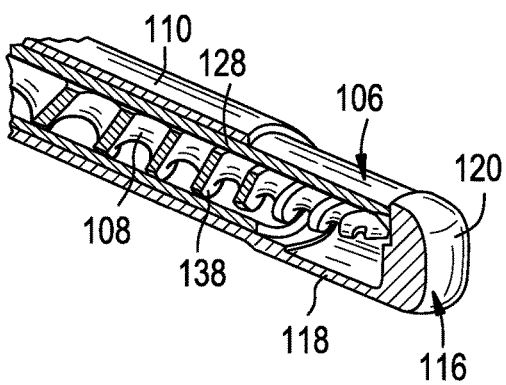
FIG. 5 is a sectional perspective view of the distal tip of the tissue removal device of FIG. 1, shown in a closed configuration.

As shown for example in FIGS. 4-5, the distal end 110*d* of the outer shaft 110 can extend to a footplate 116. The footplate can be formed integrally with the outer shaft 110, or can be a separate component coupled to the outer shaft, e.g., by a welded or snap-fit connection. The footplate 116 can include a base portion 118 and an end portion 120 that together define a hook-shaped or L-shaped structure. The end portion 120 of the footplate 116 can be disposed at a selected distance from the distal end 110*d* of the outer shaft 110 to define a tissue opening 122. Accordingly, tissue can be inserted into the tissue opening 122 to position the tissue between a cutting surface 124 of the blade 106 and an anvil surface 126 of the footplate 116. The footplate 116 can include a blunt or atraumatic distal-facing surface, which can reduce or prevent tissue irritation during use. In some embodiments, the size of the tissue opening 122 can be adjustable, e.g., by moving the footplate 116 longitudinally relative to the outer shaft 110 to alter the distance between the anvil surface 126 and the distal end 110*d* of the outer shaft. To facilitate such movement, the footplate 116 can be coupled to the outer shaft 110 by a threaded connection, a ratchet and pawl connection, or other connection that allows adjustment of the tissue opening 122 length.

The blade 106 can be slidably disposed within the outer shaft 110 such that the blade is configured to translate longitudinally relative to the outer shaft, e.g., in a reciprocating manner. The blade 106 can include an elongate body portion 128. The body portion 128 can be cylindrical or can form a section of a cylinder. A distal-most tip of the blade 106 can define a sharpened cutting surface 124 configured to shear tissue as the blade is advanced through the tissue. The cutting surface 124 can be made extremely sharp to slice through tissue with minimal smearing or compressing of the tissue. The cutting surface 124 can be of varying degrees of sharpness (e.g., razor sharp, blunt, or degrees of sharpness therebetween). The cutting surface 124 can be tapered, or can define one or more teeth. The cutting surface 124 can be received onto the footplate 116 or into a recess in the footplate. The cutting surface 124 can be formed from any of a variety of materials, such as metals including stainless steel. The cutting surface 124 can have a Rockwell hardness ranging from about 58 $R_C$ to about 65 $R_C$. The cutting surface 124 can be coated with materials to enhance ease of cutting through the tissue (lubricity) and life (durability). Exemplary materials include titanium, chromium, platinum, iron oxides, anodized surfaces, and/or combinations thereof. The cutting surface 124 can extend completely around the circumference of the cylindrical blade body 128, or can form less than an entire section of a cylinder (e.g., approximately 110 degrees to 180 degrees of a cylinder). The blade 106 can be cannulated to allow passage of severed tissue therethrough towards the proximal end of the device 100.

As shown in FIGS. 4-5, the blade 106 can be movable between a "retracted" or "open" position and an "advanced" or "closed" position. In the retracted position, shown in FIG. 4, the distal cutting surface 124 of the blade 106 is spaced a distance apart from the anvil surface 126 of the footplate 116, allowing tissue to be positioned within the tissue opening 122. In the advanced position, shown in FIG. 5, the blade 106 is advanced longitudinally with respect to the outer shaft 110 such that the distal cutting surface 124 of the blade is brought into contact with the anvil surface 126 of the footplate 116, or into close proximity to the anvil surface, to sever or cut tissue disposed between the blade and the footplate.

Figure 6:
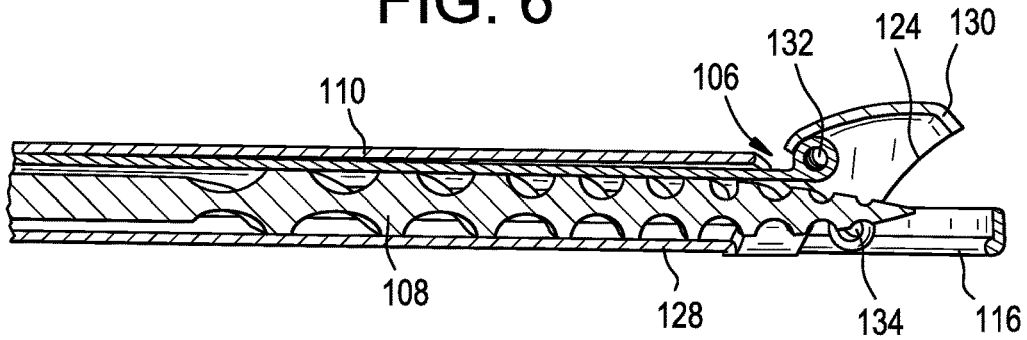
FIG. 6 is a sectional side view of the distal tip of the tissue removal device of FIG. 1, shown with a basket type blade.
Figure 7:
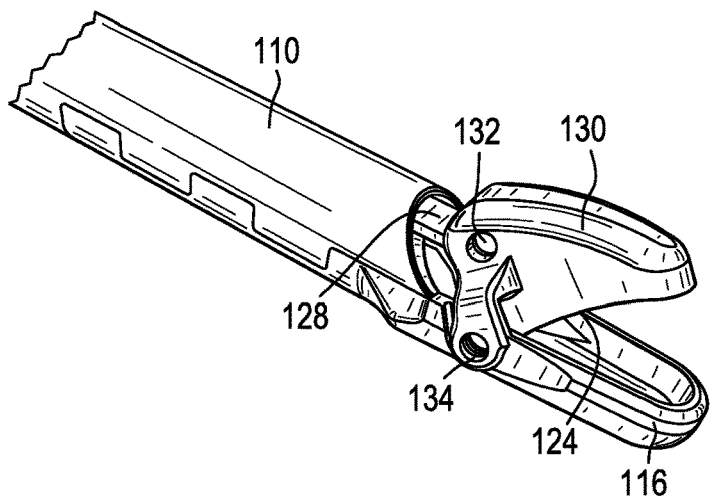
FIG. 7 is a perspective view of the distal tip of the tissue removal device of FIG. 1, shown with a basket type blade.

It will be appreciated that the blade 106 can have various other configurations. For example, as shown in FIG. 6, the device 100 can include a basket-type cutting head 130. An outer perimeter of the cutting head 130 can define the cutting surface 124. The cutting head 130 can be pivotally coupled to the reciprocating body portion 128 of the blade 106 via a first pivot pin 132 and to the footplate 116 by a second pivot pin 134. In use, the body portion 128 can be reciprocated longitudinally with respect to the outer shaft 110 to open and close the cutting head 130.

The "bite size" of the blade 106 and the geometry of the cutting surface 124 or the tissue opening 122 can be tailored to achieve the desired properties of the cut tissue. For example, the device 100 can be optimized to produce cut tissue having a size or shape that is most efficient for transfer through the outer shaft 110, auger 108, and collection chamber 112, or for subsequently packing the cut tissue into a fusion cage or other device. The device 100 can be designed to produce cut bone fragments that fit within the orifice or gaps of a fusion cage, or within a cannulated dispenser for filling screws or for direct bony injections (e.g., filling lateral mass bone holes or defects, vertebral body augmentation, and so forth).

As shown in FIGS. 3-6, the auger 108 can include an elongate shaft having a proximal end 108*p* and a distal end 108*d*. The proximal end 108*p* of the auger 108 can include one or more flats or other engagement features to allow the auger 108 to be rotationally fixed relative to an auger drive sub-assembly 136, as described further below. The distal end 108*d* of the auger 108 can include features for guiding or urging tissue proximally through the outer shaft 110 after the tissue is cut by the blade 106. For example, the auger shaft 108 can include a helical external thread 138 that that is effective to push tissue proximally along the outer shaft 110 as the auger 108 rotates. The thread 138 can extend along the entire auger 108 or only along a portion thereof (e.g., along a distal-most portion of the auger shaft).

The auger 108 can be longitudinally fixed with respect to the outer shaft 110. Alternatively, as shown in FIGS. 4-5, the auger 108 can be longitudinally movable with respect to the outer shaft 110. For example, the auger 108 can be configured to reciprocate longitudinally with respect to the outer shaft 110, either in concert with the reciprocating blade 106 or independently.

In the illustrated embodiment, the auger 108 tapers at the distal end 108*d* to a sharpened tip. It will be appreciated, however, that various other configurations can be used. For example, the distal end 108*d* of the auger 108 can define a blunt surface with milling features formed thereon to grind up severed tissue.

Figure 8:
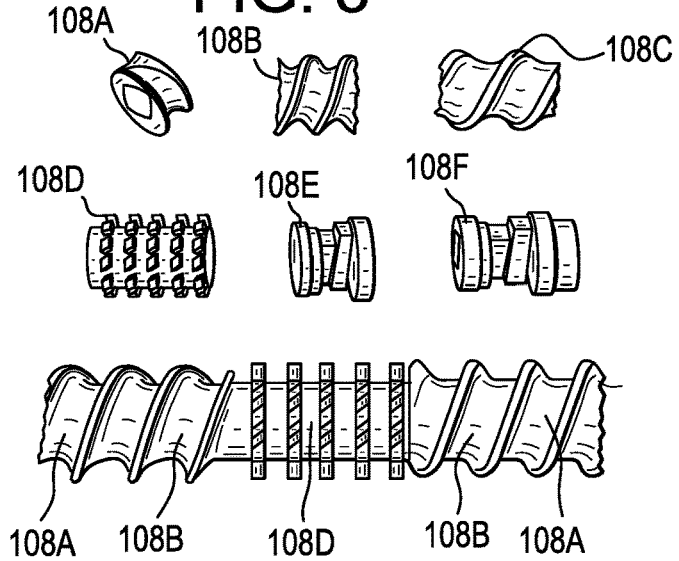
FIG. 8 is a side view of various auger shaft components for use in the tissue removal device of FIG. 1.

The auger 108 can have an exterior profile that varies along the length of the auger shaft. The specific profile can be selected based on the properties desired of the tissue to be harvested (e.g., particle size, viscosity, and so forth). FIG. 8 illustrates various auger shaft profiles that can be used. As shown, auger shaft segments 108A-F can have varying thread pitches, cam lobes, toothed discs, and other features configured to cut, grind, and/or mix tissue. The auger shaft segments 108A-F can be selected and configured to pulverize the excised tissue, to "scrub" bone tissue fragments to remove soft tissue therefrom, and/or to mince the bone tissue into the desired size or shape. The auger shaft segments 108A-F can be modular and can be assembled from a kit for a particular application, e.g., as shown in the lower portion of FIG. 8 with illustrates an assemblage of shaft segments 108A, 108B, 108D, 108B, and 108A (from left to right). The device 100 can be supplied with a plurality of augers 108 having different exterior profiles, and the auger desired for a particular procedure can be installed by the end user prior to use.

Figure 9:
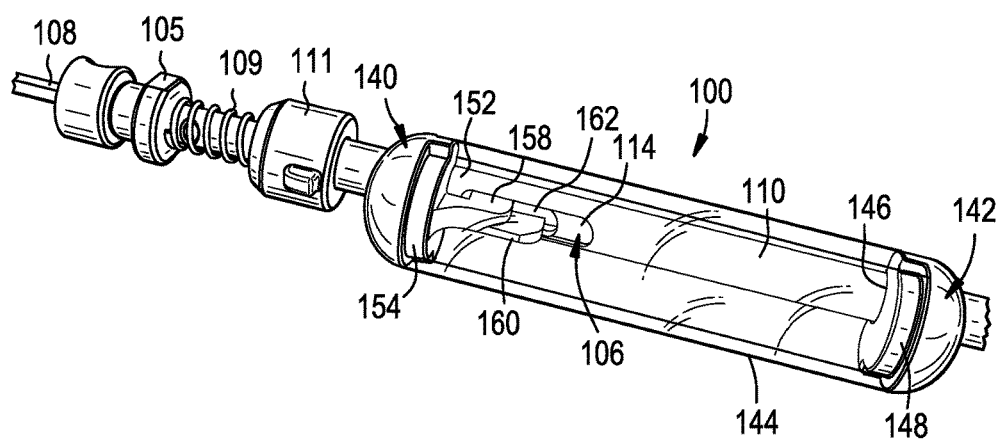
FIG. 9 is a perspective view of the tissue collection chamber of the device of FIG. 1.
Figure 10:
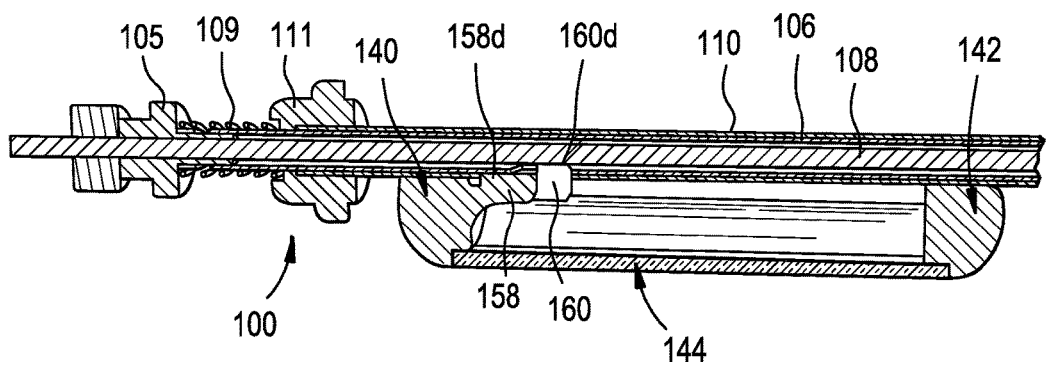
FIG. 10 is a sectional side view of the tissue collection chamber of the device of FIG. 1.

The tissue collection chamber 112 is shown in greater detail in FIGS. 9-10. As shown, the chamber 112 can be defined by a proximal end cap 140, a distal end cap 142, a chamber housing 144, and an exterior surface of the outer shaft 110. The chamber 112 can define a closed volume into which tissue severed by the blade 106 can be directed. Tissue collected in the chamber 112 can later be retrieved and disposed of or used for other portions of a surgical procedure (e.g., as bone graft material for packing a fusion cage).

The distal end cap 142 can be generally cylindrical and can define a recess 146 configured to receive the outer shaft 110. The distal end cap 142 can be attached to the outer shaft 110 using various mechanisms (e.g., a snap-fit engagement) to form a seal between the distal end cap and the outer shaft. The distal end cap 142 can also define a recessed seat 148 that receives a semi-cylindrical distal tab 150 of the chamber housing 144. The chamber housing 144 can be permanently attached to the distal end cap 142, e.g., via an adhesive or welding, or can be selectively attachable thereto, e.g., via an interference or snap-fit connection, threads, etc.

The proximal end cap 140 can be generally cylindrical and can define a recess 152 configured to receive the outer shaft 110. The proximal end cap 140 can be attached to the outer shaft 110 using various mechanisms (e.g., a snap-fit engagement, threads, etc.) to form a seal between the proximal end cap and the outer shaft. The proximal end cap 140 can also define a recessed seat 154 that receives a semi-cylindrical proximal tab 156 of the chamber housing 144. The chamber housing 144 can be permanently attached to the proximal end cap 140, e.g., via an adhesive or welding, or can be selectively attachable thereto, e.g., via an interference or snap-fit connection, threads, etc.

The proximal end cap 140 can be configured to guide tissue moving through the outer shaft 110 into the collection chamber 112. For example, the proximal end cap 140 can include a cantilevered beam that defines first and second prongs 158, 160. The first prong 158 can include a distal end 158*d* that extends through an opening 114 formed in the sidewall of the outer shaft 110. The distal end 158*d* can define a wiping surface that contacts or approximates the reciprocating blade 106 to wipe material from the blade and guide the material into the collection chamber 112. The second prong 160 can include a distal end 160*d* that extends up through the opening 114 formed in the outer shaft 110 and through an opening 162 formed in the sidewall of the reciprocating blade 106. The distal end 160d can define a wiping surface that contacts or approximates the rotating auger shaft 108 to wipe material from the auger shaft and guide the material into the collection chamber 112. The openings 114, 162 in the outer shaft 110 and the blade 106 can be aligned to allow the distal end 160d of the second prong 160 to extend therethrough. The opening 162 formed in the blade 106 can be elongated such that it has a longitudinal length that is greater than a longitudinal length of the distal portion 160d of the second prong 160. Accordingly, the blade 106 can be free to reciprocate longitudinally relative to the second prong 160 when the second prong is inserted through the opening 162.

The tissue collection chamber 112 can include a piston or auger disposed therein for dispensing collected tissue from the chamber, or can allow for the use of a separate piston or auger. The tissue collection chamber 112 can include one or more internal blades (e.g., rotatably driven via a gear linkage to the auger shaft 108 or another rotating component of the device) configured to further mince tissue disposed in the chamber to attain a desired particle size or consistency. The tissue collection chamber 112 can include one or more mixing shafts (e.g., rotatably driven via a gear linkage to the auger shaft 108 or another rotating component of the device) configured to mix the collected tissue, optionally with one or more additives such as platelet rich plasma (PRP) or other biologics that enhance tissue flow rate or biologic activity.

The collection chamber 112 can be selectively openable and/or removable from the device 100. For example, the proximal end cap 140, distal end cap 142, and chamber housing 144 can be separated as a single unit from the outer shaft 110. By way of further example, the chamber housing 144 can be separated from the proximal and distal end caps 140, 142 while the end caps remain coupled to the outer shaft 110. The proximal end cap 140, distal end cap 142, and chamber housing 144 can be separate components as shown, or two or more of said components can be integrally formed as a single monolithic unit.

In some embodiments, the tissue collection chamber 112 can be omitted. For example, the tissue collection chamber 112 can be replaced with a tube having a first end that is in fluid communication with the opening 114 formed in the outer shaft 110 and a second end that drains into a tissue collection tray or container. As another example, the opening 114 in the outer shaft 110 can be omitted and cut tissue can be collected within the outer shaft. The outer shaft 110 can include a plunger configured to slide within the outer shaft to eject collected tissue from the outer shaft. The plunger can be manually actuated or driven by a powered handle.

Collection of tissue within the shaft 110 of the device 100 and/or within a tissue collection chamber 112 can advantageously eliminate or reduce the need for the user to repeatedly remove and reinsert the device 100 from the patient to clear tissue therefrom.

Figure 11:
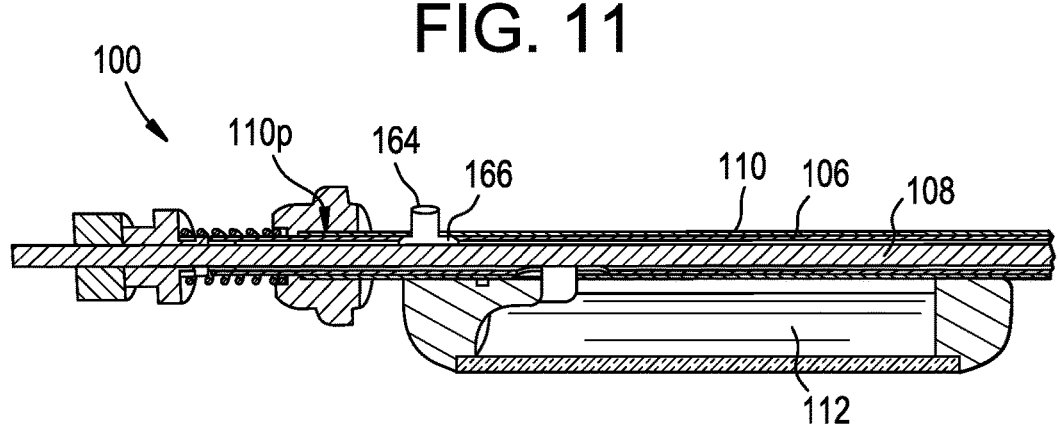
FIG. 11 is a sectional side view of the device of FIG. 1, shown with an aspiration port.

The device 100 can include an aspiration feature to help ensure that cut tissue moves proximally through the device or to pull tissue into the tissue opening 122. For example, as shown in FIG. 11, the outer shaft 110 can include an aspiration port 164 adjacent a proximal end 110p thereof to which a vacuum source can be applied to the outer shaft to help draw tissue proximally through the outer shaft. The aspiration port 164 can be aligned with an elongated opening 166 formed in the blade 106 such that a vacuum can be continuously applied to the interior of the blade as the blade reciprocates longitudinally within the outer shaft 110. By way of further example, the aspiration port can be formed in the collection chamber 112 to allow the aspiration to be pulled through the collection chamber.

Figure 12:
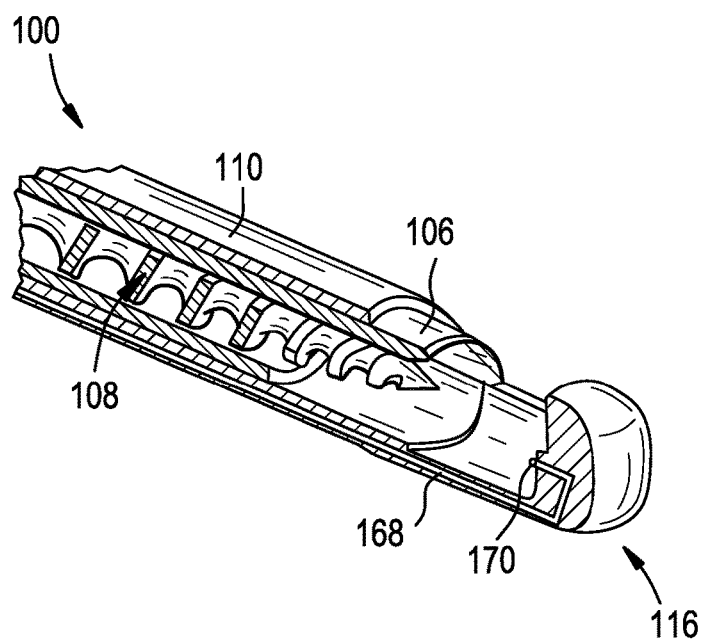
FIG. 12 is a sectional perspective view of the device of FIG. 1, shown with an irrigation lumen.

As shown in FIG. 12, the device 100 can include an irrigation lumen 168 configured to supply a fluid to an interior of the device. The irrigation lumen 168 can include a fluid inlet port (not shown), which can be formed at a proximal end 110p of the outer shaft 110, and one or more fluid outlet ports 170. In the illustrated embodiment, the irrigation lumen 168 is formed in a sidewall of the outer shaft 110. In other embodiments, however, the irrigation lumen 168 can be an independent tube disposed within the outer shaft 110 or along an exterior of the outer shaft, or can be formed within or attached to a surface of the blade 106 or the auger 108, or the annular gap between the blade 106 and the outer shaft 110 can define the irrigation lumen. In the illustrated embodiment, the irrigation lumen 168 includes a single fluid outlet port 170 formed in a proximal-facing surface of the footplate 116. It will be appreciated, however, that the irrigation lumen 168 can include any number fluid outlet ports that can be positioned in any of a variety of locations. For example, the irrigation lumen 168 can include a plurality of fluid outlet ports spaced apart from one another along a length of the outer shaft 110. By way of further example, the irrigation lumen 168 can include a fluid outlet port disposed adjacent the distal end of the auger 108 to lubricate and wash the helical thread of the auger. As yet another example, the irrigation lumen 168 can include a fluid outlet port disposed adjacent the proximal end cap 140 of the tissue collection chamber 112 to lubricate and wash the wiping surfaces of the first and second prongs 158, 160 and to wash tissue down into the chamber.

The fluid inlet port can be in fluid communication with a source of irrigation fluid. Exemplary irrigation fluids include saline, water, and various other lubricants or additives that enhance tissue flow through the device and into the collection chamber. The irrigation fluid can be or can include sodium hypochlorite, calcium hydroxide, hydrogen peroxide, or other additives configured to dissolve soft tissue. Accordingly, severed bone material can be cleansed of soft tissue as the bone material moves through the device 100 to the collection chamber 112, which can make the bone material more suitable for subsequent use (e.g., in packing a fusion cage or filling boney voids in the anatomy). The irrigation fluid can include one or more additives such as platelet rich plasma (PRP) or other biologics that enhance tissue flow rate or biologic activity.

Figure 13:
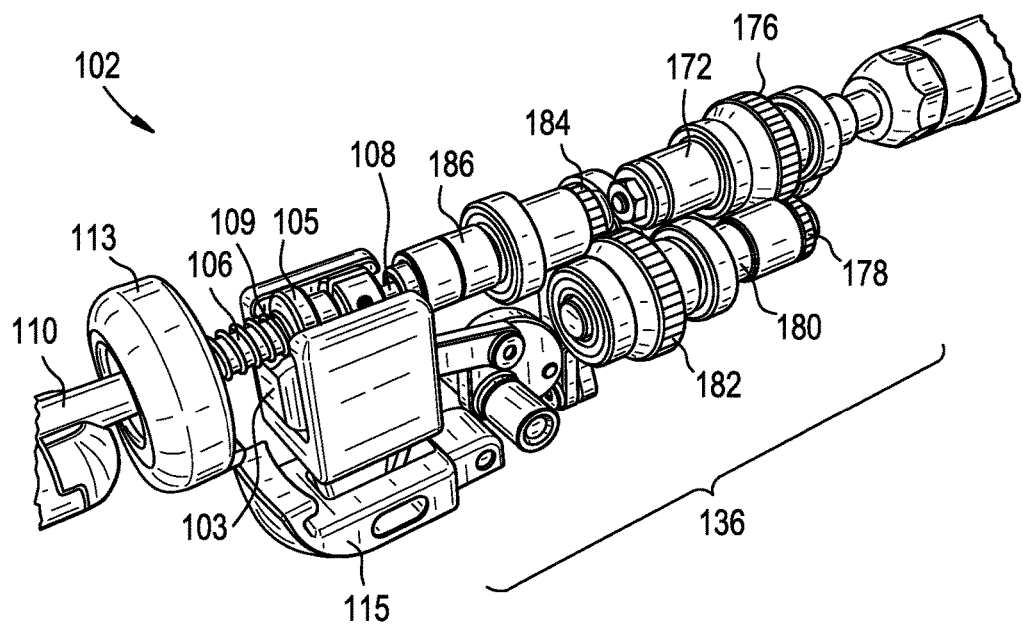
FIG. 13 is a perspective view of the proximal drive assembly of the device of FIG. 1, shown with the outer shell and support elements omitted.
Figure 14:
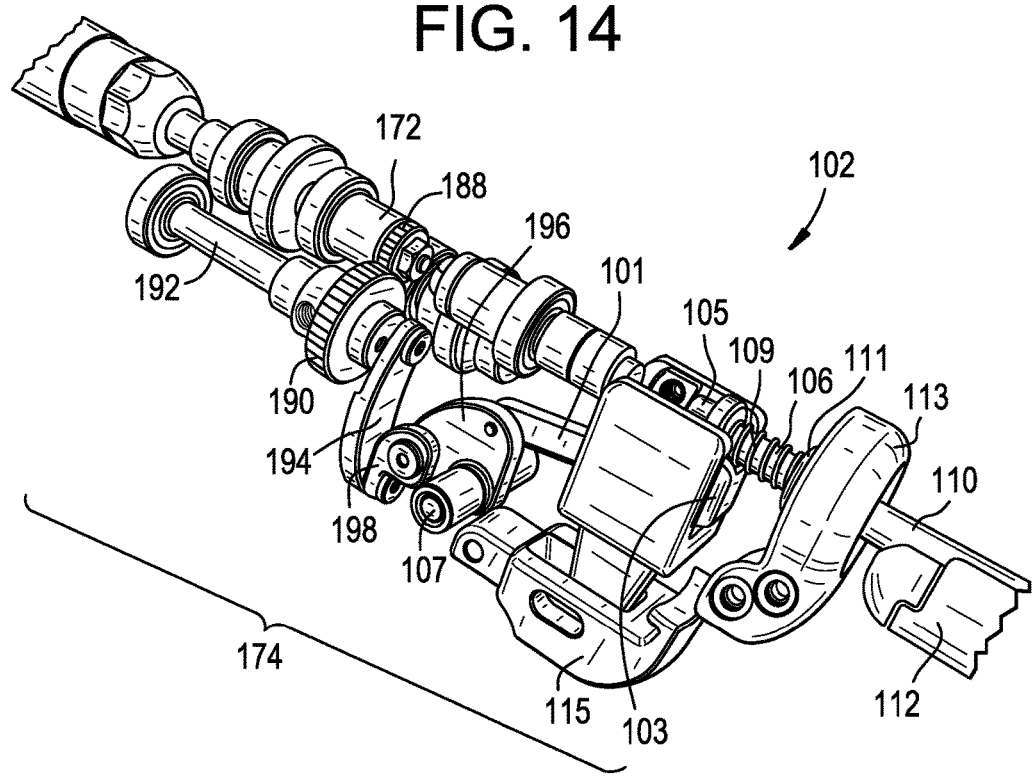
FIG. 14 is another perspective view of the proximal drive assembly of the device of FIG. 1, shown with the outer shell and support elements omitted.

The internal components of an exemplary proximal drive assembly 102 are shown in FIGS. 13-14. The drive assembly 102 can include an input shaft 172 configured to be coupled to a rotating drive system (e.g., an electric or pneumatic drill or driver, such as the one shown in FIG. 15). An auger drive sub-assembly 136 can convert rotation of the input shaft 172 to rotation of the auger 108. The auger drive sub-assembly 136 can be configured to scale the rotation of the input shaft 172 such that the auger 108 rotates at a different rate than the input shaft (i.e., faster or slower than the input shaft). A blade drive sub-assembly 174 can convert rotation of the input shaft 172 to reciprocating movement of the blade 106.

Referring to FIG. 13, the auger drive sub-assembly 136 can include a first gear 176 on the input shaft 172 that drives a corresponding second gear 178 on an intermediate auger shaft 180. The intermediate auger shaft 180 can include a third gear 182 that drives a corresponding fourth gear 184 on an auger output shaft 186. The proximal end 108p of the auger 108 can be received in a keyed opening formed in the distal end of the output shaft 186, such that rotation of the auger output shaft is effective to rotate the auger. In operation, rotation of the input shaft 172 is effective to rotate the intermediate shaft 180 via interaction between the first and second gears 176, 178. This rotation of the intermediate shaft 180 results in rotation of the output shaft 186, and the auger 108 coupled thereto, via interaction between the third and fourth gears 182, 184. The geometry of the first, second, third, and fourth gears 176, 178, 182, 184, including their respective diameters, numbers of teeth, etc., can be selected to achieve the desired rate of auger rotation. In an exemplary embodiment, the gears are effective to convert the input shaft 172 rotation to an output shaft 186 rotation of approximately 350 rpm.

Referring to FIG. 14, the blade drive sub-assembly 174 can include a fifth gear 188 on the input shaft 172 that drives a corresponding sixth gear 190 on an intermediate blade shaft 192. The intermediate blade shaft 192 can include a first linkage bar 194 eccentrically coupled thereto. The first linkage bar 194 can be coupled to a proximal end of a rocker arm 196 via a right angle pivot 198. A distal end of the rocker arm 196 can be coupled to a second linkage bar 101, which in turn can be coupled to a forked sled 103 that cradles a blade collar 105. The blade collar 105 can be longitudinally-fixed with respect to the blade 106. In operation, rotation of the input shaft 172 is effective to rotate the intermediate blade shaft 192 via interaction between the fifth and sixth gears 188, 190. As the intermediate blade shaft 192 rotates, the attachment point between the shaft and the linkage bar 194 orbits the central longitudinal axis of the shaft 192, alternately raising and lowering the linkage bar and, as a result, alternately rotating the rocker arm 196 clockwise and counterclockwise about an axle 107. Clockwise rotation of the rocker arm 196 (from the perspective shown in FIG. 14) drives the second linkage bar 101 distally, which pushes the sled 103, collar 105, and blade 106 distally. Counterclockwise rotation of the rocker arm 196 (from the perspective shown in FIG. 14) pulls the second linkage bar 101 proximally, which pulls the sled 103, collar 105, and blade 106 proximally with assistance from a bias spring 109 disposed between the collar and a ring 111 fixedly coupled to the outer shaft 110 of the device 100. The ring 111 can include radially-projecting ears or other features for aligning the ring (and by extension the outer shaft 110 and tissue opening 122) with a distal nose portion 113 of the proximal drive assembly's outer housing 117.

Accordingly, the blade drive sub-assembly 174 can convert rotation of the input shaft 172 to reciprocating movement of the blade 106. The geometry of the various components of the blade drive sub-assembly 174 can be selected to achieve the desired blade 106 actuation rate (e.g., the number of chomps or punches per unit time). In some embodiments, the device 100 is configured to actuate the blade 106 between one and ten times per second, between one and five times per second, between two and four times per second, and/or approximately three times per second. The actuation rate can be selected based on typical user reaction times to ensure that the device 100 is comfortable and safe to operate. The actuation rate can also be made sufficiently slow to allow a single blade 106 actuation to be easily achieved by briefly actuating the rotary drive system.

The auger drive sub-assembly 136 and the blade drive sub-assembly 174 can include any of a variety of bearings, washers, bushings, supporting elements, etc. to facilitate the operation described above. For clarity of illustration, one or more of these components are not shown in FIGS. 13-14, though the structure and function of these components will be readily appreciated by those having ordinary skill in the art in view of the teachings herein. The internal components of the proximal drive assembly 102 can be enclosed within an outer housing or clamshell case 117, as shown in FIG. 1.

The elongate cutting assembly 104 (e.g., the outer shaft 110, blade 106, auger 108, and tissue collection chamber 112) can be easily detachable from the proximal drive assembly 102. This can allow for selective detachment/reattachment of the cutting assembly 104 for quick and easy cleaning, replacement, etc. The various components of the devices described herein can be reusable or disposable. In some embodiments, the proximal drive assembly 102 can be reusable, while the distal cutting assembly 104 can be a disposable unit adapted for use with a single patient or in a single procedure. The distal cutting assembly 104 can be easily loaded into the proximal drive assembly 102, for example by snapping and locking into place. Any of a number of snap/lock mechanisms can be utilized. In some embodiments, the blade collar 105 can snap into the sled 103. The sled 103 can translate orthogonally away from the axis L of the device 100 and then back to capture the blade collar 105. A lever 115 can be used to translate the sled orthogonally away and then lock it back.

Figure 15:
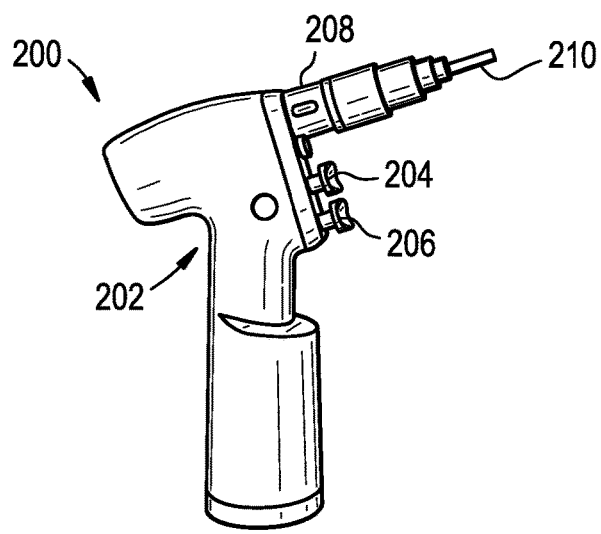
FIG. 15 is a perspective view of a driver tool.

FIG. 15 illustrates an exemplary embodiment of a driver tool 200 that can be used with any of the devices disclosed herein. The driver tool 200 generally includes a handle portion 202 with first and second actuation buttons 204, 206, a non-rotating mating portion 208 configured to mate the driver tool 200 with the housing 117 of the proximal drive assembly 102, and a rotating component 210 configured to mate with and rotate the input shaft 172 of the device 100. The rotating component 210 can be driven by a motor and a power source (e.g., a battery) disposed in the driver tool 200. In some embodiments, one of the actuation buttons 204, 206 can be depressed to rotate the rotating component 210 clockwise and the other of the actuation buttons can be depressed to rotate the rotating component counterclockwise. Other exemplary driver tools include the Colibri II System (a compact and modular Li-Ion-battery-driven power tool) available from DePuy Synthes.

Figure 16:
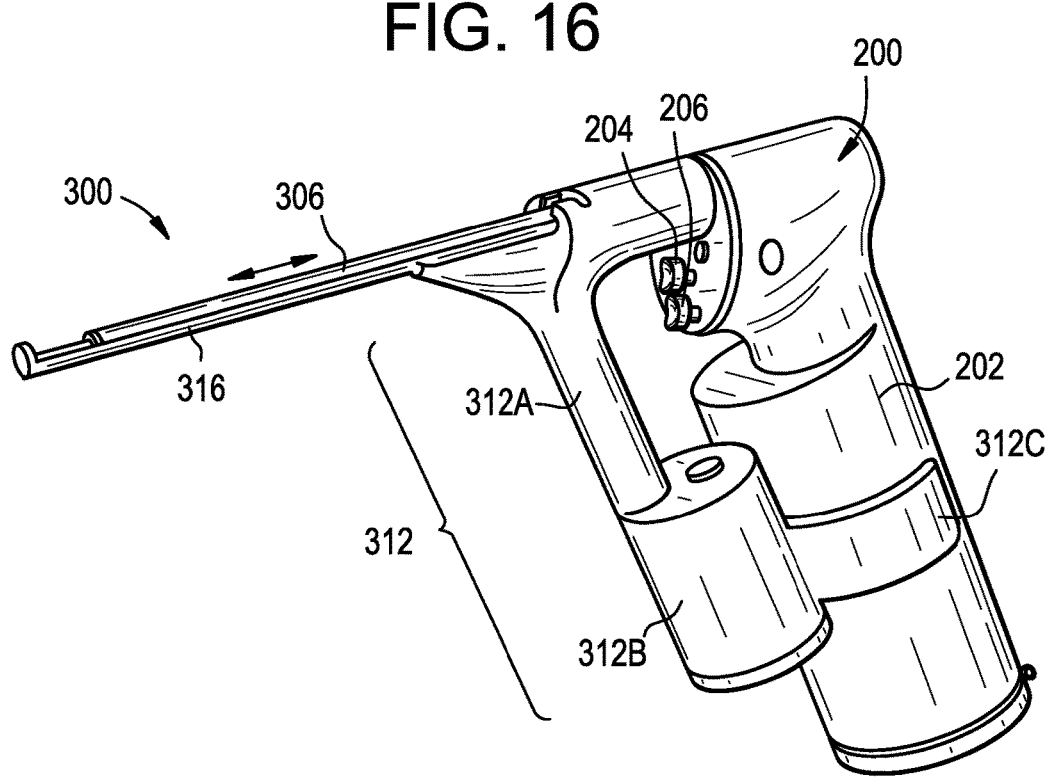
FIG. 16 is a perspective view of a tissue removal device.

The driver tool 200 is shown with another exemplary embodiment of a tissue removal device 300 in FIG. 16. Except as indicated below and as will be readily apparent to one having ordinary skill in the art, the structure and function of the device 300 can be substantially similar to the structure and function of the device 100 described above. Accordingly, a detailed description is omitted here for the sake of brevity. As shown, the outer shaft of the device 300 can be omitted and the device can instead include an elongated footplate 316 and an exposed reciprocating blade 306. The exposed blade 306 can be easier to replace or disassemble for cleaning, sharpening, and so forth. The tissue collection chamber 312 of the device 300 can include an elongated neck portion 312A that extends down from the shaft of the device, substantially perpendicular to a longitudinal axis of the reciprocating blade 306. The tissue collection chamber 312 can include a substantially cylindrical canister portion 312B adjacent the neck portion 312A. The canister portion 312B can include first and second arms 312C that define a space therebetween sized to receive the handle portion 202 of the driver tool 200. Accordingly, the tissue collection chamber 312 can snap onto the handle portion 202 or otherwise attach to the handle portion. The geometry of the tissue collection chamber 312 can provide an ergonomic solution for the user, defining an opening through which the user's fingers can be inserted to actuate the controls 204, 206 of the driver tool 200. The driver tool 200 and the devices 100, 300 described herein can provide a compact, self-contained solution for tissue removal with reduced user input force and strain and improved ergonomics. In some embodiments, the device 100, 300 and the driver tool 200 can be a standalone system with no external attachment to a mains current supply or a pneumatic source.

The devices disclosed herein can be used in any of a variety of medical, surgical, and other procedures to cut, grind, gnaw, chip, or sever tissue or other materials. For example, the devices disclosed herein can be used to cut bone tissue during spinal surgery, including posterior decompression, laminectomy, laminotomy, and posterior disc access procedures.

In an exemplary method, a distal cutting assembly 104 having the properties (e.g., diameter, length, cutting window size, blade type, blade sharpness, auger type, etc.) desired for a particular procedure can be selected from among a plurality of distal cutting assemblies and coupled to the proximal drive assembly 102. The proximal drive assembly 102 can be coupled to a powered driver 200 such that the input shaft 172 of the proximal drive assembly is rotated when the driver is actuated.

Once assembled, the distal end 110d of the elongate outer shaft 110 can be inserted through a surgical opening in a patient to position the footplate 116 and blade cutting surface 124 in proximity to tissue that is to be cut. The tissue can be positioned within the tissue opening 122, manually or with assistance from vacuum suction applied through the aspiration port 164. The user can then actuate the powered driver 200 to rotate the input shaft 172 of the proximal drive assembly 102, thereby advancing the blade 106 distally to sever the tissue disposed in the tissue opening 122. Rotation of the input shaft 172 can also be effective to rotate the auger 108 to urge the severed tissue proximally towards the tissue collection chamber 112. Vacuum suction can be applied to the interior of the shaft 110 to pull the tissue proximally. Irrigation fluid can be delivered to the interior of the shaft 110 to wash or lubricate the tissue and facilitate proximal movement. As noted above, the irrigation fluid can include various additives to dissolve or strip soft tissue from bone tissue disposed in the device.

As the input shaft 172 continues to rotate, the blade 106 can be retracted proximally to prepare for the next cutting operation. Rotation of the input shaft 172 can produce reciprocating movement of the blade 106, repeatedly cutting additional tissue as the tissue is moved into the tissue opening 122. With each successive cutting operation, tissue cut during previous operations can be pushed proximally through the shaft 110 by the newly incoming tissue, by the auger 108, and/or by the flow of irrigation fluid and/or vacuum aspiration. The user can continue to cut tissue indefinitely, without having to remove the distal end of the device 100 from the patient.

The tissue collection chamber 112 can be emptied when necessary or at any time desired by the user. Blades, mixing heads, grinding wheels, or other structures in the tissue collection chamber 112 can be used to further process collected tissue. For example, the method can include mincing tissue collected in the collection chamber 112 to a desired size or consistency. The method can also include treating the collected tissue with an additive to dissolve soft tissue or promote bioactivity. Tissue collected in the collection chamber 112 can be harvested and reused, e.g., as graft material. In some embodiments, the method can include packing tissue collected in the chamber 112 into a spinal fusion cage or other implant, before or after implanting the cage in the patient.

When use of the device 100 is completed, the distal cutting assembly 104 can be separated from the proximal drive assembly 102 and disposed of or processed for use in subsequent procedures. The proximal drive assembly 102 can likewise be disposed of or processed for use in subsequent procedures.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The devices disclosed herein and the various component parts thereof can be constructed from any of a variety of known materials. Exemplary materials include those which are suitable for use in surgical applications, including metals such as stainless steel, polymers such as PEEK, ceramics, carbon fiber, and so forth. The various components of the devices disclosed herein can be rigid or flexible. The devices can include steering features for remotely positioning the distal end of the device in proximity to target tissue. One or more components or portions of the device can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. While the devices and methods disclosed herein are generally described in the context spinal surgery, it will be appreciated that the devices and methods disclosed herein can be used in any of a variety of surgeries performed on humans or animals, and/or in fields unrelated to surgery.

Although specific embodiments have been described, it should be understood that numerous changes may be made within the spirit and scope of the concepts described.

The invention claimed is:

1. A tissue cutting device, comprising:
   a footplate;
   a blade having a cutting surface, wherein the blade is movable relative to the footplate between an open position in which a tissue opening is formed between the cutting surface and the footplate and a closed position in which the cutting surface contacts or approaches the footplate to cut tissue disposed therebetween;
   an auger disposed in a lumen of the device and configured to transport tissue cut by the blade proximally through the lumen; and
   an input shaft, wherein the input shaft is coupled to a blade drive assembly that converts rotational movement of the input shaft into reciprocating movement of the blade between the open and closed positions and wherein the input shaft is coupled to an auger drive assembly that converts the rotational movement of the input shaft into rotating movement of the auger.

2. The device of claim 1, wherein the lumen is formed in the blade.

3. The device of claim 1, wherein the lumen is formed in an outer shaft of the device, the blade being slidably disposed in the outer shaft.

4. The device of claim 1, wherein the blade includes an elongate body portion and a basket pivotally coupled to a distal end of the body portion.

5. The device of claim 1, wherein the blade includes a tubular cannulated body with a sharpened distal-facing surface that defines the cutting surface.

6. The device of claim 1, further comprising a tissue collection chamber mounted to the device and in fluid communication with the lumen.

7. The device of claim 6, wherein the tissue collection chamber is mounted to an outer shaft of the device and wherein the tissue collection chamber comprises a first prong that extends through an opening in the outer shaft to wipe tissue from the blade.

8. The device of claim 7, wherein the tissue collection chamber comprises a second prong that extends through the opening in the outer shaft and through an opening formed in the blade to wipe tissue from the auger.

9. The device of claim 1, wherein the auger drive assembly comprises a first plurality of gears configured to scale rotation of the auger relative to rotation of the input shaft.

10. The device of claim 1, wherein the blade drive assembly comprises a second plurality of gears configured to convert the rotational movement of the input shaft into longitudinal reciprocating movement of the blade.

11. The device of claim 1, wherein the blade drive assembly comprises a first linkage bar having a first end eccentrically coupled to a rotating shaft and a second end coupled to a rocker arm such that rotation of the rotating shaft alternately rotates the rocker arm clockwise and counterclockwise to alternately advance and retract the blade.

12. The device of claim 1, wherein a shaft of the auger comprises a plurality of modular sections with different profiles configured to mix, shear, or grind tissue.

13. The device of claim 1, further comprising an aspiration port through which vacuum suction can be applied to an interior of the lumen.

14. The device of claim 1, further comprising an irrigation port through which fluid can be supplied to an interior of the lumen.

15. The device of claim 1, wherein the tissue collection chamber comprises a neck portion having a longitudinal axis that extends substantially perpendicular to a longitudinal axis of the blade and a canister portion in fluid communication with the neck portion.

* * * * *